United States Patent [19]

Lin et al.

[11] Patent Number: 5,112,979

[45] Date of Patent: May 12, 1992

[54] POLYOXYALKYLENEAMINES CONTAINING TETRAALKYLPIPERIDINE FUNCTIONALITY AND THEIR USE AS LIGHT, HEAT AND OXIDATION STABILIZERS

[75] Inventors: Jiang-Jen Lin, Houston; Michael Cuscurida; Harold G. Waddill, both of Austin, all of Tex.

[73] Assignee: Texaco Chemical Company, White Plains, N.Y.

[21] Appl. No.: 619,535

[22] Filed: Nov. 29, 1990

[51] Int. Cl.$^5$ .................................. C07D 211/58
[52] U.S. Cl. .................................................. 546/244
[58] Field of Search ........................................ 546/244

[56] References Cited

U.S. PATENT DOCUMENTS

| 4,001,250 | 1/1977 | Lantzsch et al. | 546/244 |
| 4,145,512 | 3/1979 | Uhrhan et al. | 546/244 |
| 4,298,737 | 11/1981 | Lai et al. | 549/360 |
| 4,925,974 | 5/1990 | Gras | 546/244 |

FOREIGN PATENT DOCUMENTS

| 654695 | 12/1962 | Canada | 546/244 |
| 302020 | 2/1989 | European Pat. Off. | 546/244 |
| WO81/01706 | 6/1981 | PCT Int'l Appl. | 546/244 |

Primary Examiner—Kriellion S. Morgan
Attorney, Agent, or Firm—Robert A. Kulason; James J. O'Loughlin; Dominick G. Vicari

[57] ABSTRACT

A compound of the formula:

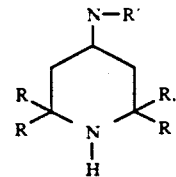

where each of the R groups are the same and include a $C_1$ to $C_4$ alkyl and R' is either

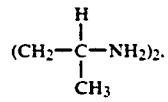

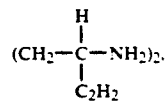

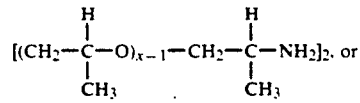

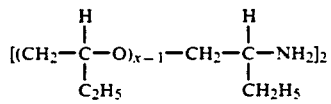

where x is a number from 2 to 10 is disclosed.

The use of the prescribed component as a light, heat and oxidation stabilizer in polyurea, polyurethane and polyurethane-urea elastomers, as well as epoxy systems, is also disclosed.

8 Claims, No Drawings

POLYOXYALKYLENEAMINES CONTAINING TETRAALKYLPIPERIDINE FUNCTIONALITY AND THEIR USE AS LIGHT, HEAT AND OXIDATION STABILIZERS

BACKGROUND OF THE INVENTION

1. Field of the Invention

This invention relates to novel polyoxyalkyleneamine compounds having tetraalkylpiperidine groups and to the use of said compounds as light, heat and oxidation stabilizers in, for instance, epoxy resins, and polyurea, polyurethane and polyurethane-urea elastomer systems.

2. Description of Background Art

Epoxy resins, and polyurea and polyurethane elastomers have wide commercial application. For instance, epoxy resins are used commercially as surface coatings, adhesives, to prepare rigid foams, as well as a variety of other applications. Polyurea and polyurethane elastomers are also used, as coatings and can be used for part production by injection molding in a closed mold or by spraying onto an open mold. In any event, systems including epoxies, polyureas and polyurethanes can exhibit poor stability when exposed to heat and/or light. The resulting degradation of the system is typically manifested by a change in color; a general loss of product integrity, such as cracking; and an adverse reduction in properties, such as tensile strength, tear strength and elongation, to name a few. Accordingly, the skilled artisan is continuously endeavoring to provide systems that exhibit stability when exposed to heat and/or light.

The use of piperidine compounds and certain derivatives thereof as light, heat, and oxidation stabilizers is well known. U.S. Pat. Nos. 4,315,859; 4,469,829; 4,528,374; 4,670,488; 4,670,489; 4,695,599; 4,695,600; 4,716,187; and 4,719,037 are illustrative in this regard.

U.S. Pat. No. 4,526,971 describes a process for producing polyalkylpiperidylamines by reductively alkylating a certain alkylated 4-aminopiperidine with a certain difunctional alcohol.

SUMMARY OF THE INVENTION

The present invention is directed to a compound of the formula:

[piperidine structure with N—R' at top, R,R substituents, and N—H]

where each of the R groups are the same and include a $C_1$ to $C_4$ alkyl and R' is either $$(CH_2-\underset{\underset{CH_3}{|}}{\overset{\overset{H}{|}}{C}}-NH_2)_2.$$

$$(CH_2-\underset{\underset{C_2H_5}{|}}{\overset{\overset{H}{|}}{C}}-NH_2)_2.$$

$$[(CH_2-\underset{\underset{CH_3}{|}}{\overset{\overset{H}{|}}{C}}-O)_{x-1}-CH_2-\underset{\underset{CH_3}{|}}{\overset{\overset{H}{|}}{C}}-NH_2]_2$$

or $$[(CH_2-\underset{\underset{C_2H_5}{|}}{\overset{\overset{H}{|}}{C}}-O)_{x-1}-CH_2-\underset{\underset{C_2H_5}{|}}{\overset{\overset{H}{|}}{C}}-NH_2]_2.$$

where x is a number from 2 to 10. Most preferably, R is a methyl radical.

Applicants have advantageously discovered that the compound of this invention, when employed in polyurea, polyurethane or polyurethane-urea elastomers or in epoxy systems, exhibits improved stability towards light, heat and/or oxidation.

DESCRIPTION OF THE PREFERRED EMBODIMENTS

The novel polyoxyalkyleneamine compounds of this invention are represented by the structure:

[piperidine structure with N—R' at top, R,R substituents, and N—H]

where each of the R groups are the same and include a $C_1$ to $C_4$ alkyl, most preferably a methyl radical, and R' is either $$(CH_2-\underset{\underset{CH_3}{|}}{\overset{\overset{H}{|}}{C}}-NH_2)_2.$$

$$(CH_2-\underset{\underset{C_2H_5}{|}}{\overset{\overset{H}{|}}{C}}-NH_2)_2.$$

$$[(CH_2-\underset{\underset{CH_3}{|}}{\overset{\overset{H}{|}}{C}}-O)_{x-1}-CH_2-\underset{\underset{CH_3}{|}}{\overset{\overset{H}{|}}{C}}-NH_2]_2$$

or $$[(CH_2-\underset{\underset{C_2H_5}{|}}{\overset{\overset{H}{|}}{C}}-O)_{x-1}-CH_2-\underset{\underset{C_2H_5}{|}}{\overset{\overset{H}{|}}{C}}-NH_2]_2.$$

where x is a number from 2 to 10.

In one embodiment, where R' is $$(CH_2-\underset{\underset{CH_3}{|}}{\overset{\overset{H}{|}}{C}}-NH_2)_2.$$

the compound of the present invention is prepared in a two-step reaction sequence. Specifically, in the first step, 2,2,6,6-tetraalkyl-4-aminopiperidine (TAAP) is reacted with propylene oxide to form the propylene oxide adduct shown below as (I):

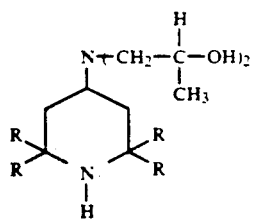

In an alternative embodiment, the first step can include reacting TAAP with 1,2-butylene oxide to form the butylene oxide adduct shown below as (II):

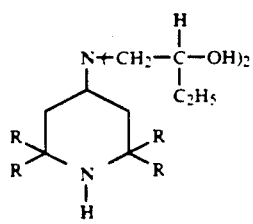

The alkyl group in the TAAP can be $C_1$ to $C_4$ alkyl and, most preferably, is a methyl radical. The reaction described above can take place at a temperature of about 100° C. to about 180° C. In a preferred embodiment, the reaction mixture is vacuum and nitrogen stripped at a temperature of about 125° C. to about 150° C. to remove any unreacted propylene oxide.

Advantageously, the reaction that takes place in step 1 occurs without the aid of a catalyst.

In step 2 (the amination step) of the two-step reaction sequence, the propylene oxide adduct identified above as (I) is reacted with ammonia, in the presence of a catalyst composition, to produce the polyoxyalkyleneamine compound shown below as (III):

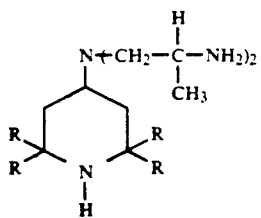

Similarly, the amination step can include reacting the butylene oxide adduct identified above as (II) with ammonia, under the same conditions, to produce the polyoxyalkyleneamine compound shown below as (IV):

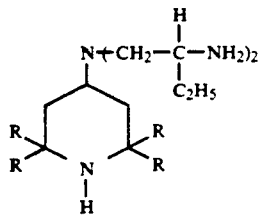

In the reductive amination reaction described above as step 2, the propylene oxide adduct (I) or butylene oxide adduct (II) is preferably reacted with a molar excess of ammonia, that is, from about 25 to about 60 weight percent ammonia, for better conversion of OH to $NH_2$. Also, by using a molar excess of ammonia, the amount of side reactions, such as secondary amine formation, will be minimized. The reaction is typically carried out in the presence of hydrogen to prevent deactivation of the catalyst.

The catalyst used in the reaction described above as step 2 can include any amination catalyst. The nickel catalysts are preferred, with Raney ® Ni (See U. S. Pat. No. 4,766,245), nickel-copper-chromium and nickel-copper-chromium-molybdenum being particularly preferred.

The propylene oxide adduct (I) or butylene oxide adduct (II) is reacted with the ammonia and hydrogen, in step 2, at a temperature of about 180° C. to about 250° C. and at a pressure of about 500 to about 4000 psig.

In another embodiment, where R' is

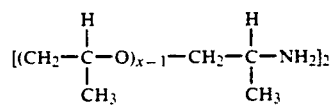

or

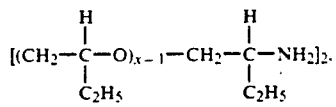

the compound of the present invention is prepared in a manner similar to that discussed above. More particularly, the propylene oxide adduct (I) or butylene oxide adduct (II) are prepared in the same manner. In accordance with this embodiment, however, the adduct (I) or (II) is further reacted with an additional amount of propylene oxide or, where appropriate, butylene oxide (e.g., x moles), prior to performing the amination reaction, to produce the intermediate product shown below as (V) or, where the butylene oxide adduct (II) is used, (VI):

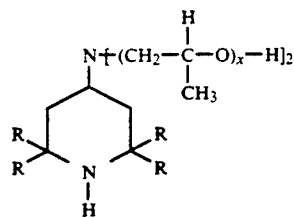

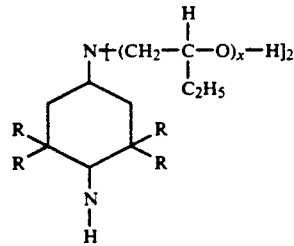

where x is the number of moles of propylene oxide or butylene oxide reacted with the propylene oxide adduct (I) or butylene oxide adduct (II).

It has been discovered that lower molecular weight products, for example where X is 2 to 10, exhibit better UV stabilizing properties.

In the reaction described immediately above, it is desirable to employ a basic alkoxylation catalyst. Typical alkoxylation catalysts include alkali methoxides or hydroxides, such as potassium hydroxide, sodium hydroxide, potassium methoxide, sodium methoxide and cesium hydroxide.

It is also desirable to add a chemical adsorbent or an acid to the reaction product before recovering same to adsorb any alkali ions resulting from use of the catalyst. Such chemical adsorbents can include magnesium silicate, activated alumina and acid clay. Acids that can be used include, by way of illustration, oxalic, sulfuric and phosphoric. Inhibitors, such as di-t-butyl-p-cresol and other hindered phenols can also be added to stabilize the intermediate reaction product.

In this embodiment, the intermediate reaction product (V) or (VI) is next reacted (aminated) with ammonia and hydrogen and in the presence of a catalyst composition to produce the polyoxyalkyleneamine compound shown below as (VII), where intermediate reaction product (V) is used, or (VIII) where intermediate reaction product (VI) is used:

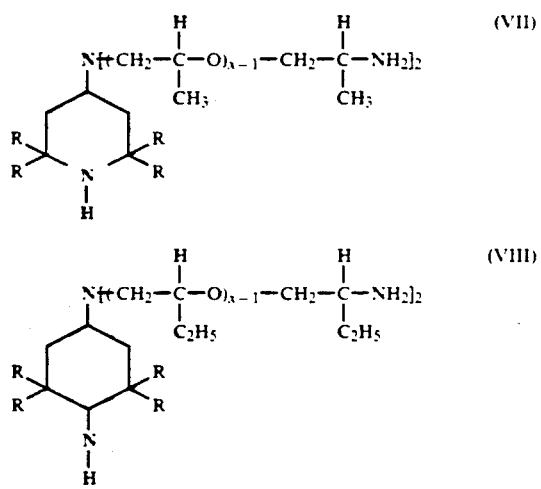

This amination reaction is conducted in the same manner and under the same conditions as described above in connection with the amination of the propylene oxide adduct (I) or butylene oxide adduct (II).

The novel polyoxyalkyleneamine compound of the present invention is generally characterized by having a total acetylatables value of from about 1 to about 7.5 meg/g and, more particularly, from about 1.5 to about 7.5 meq/g. The present compound also has a total amine value of from about 1 to about 15 meq/g, a primary amine value of from about 0.5 to about 7.35 meq/g, a tertiary amine value of from about 0.5 to about 3.7 meq/g and a molecular weight of about 270 to about 1500. As stated above, lower molecular weight compounds, for instance those having a molecular weight of from about 270 to about 1000, exhibit superior UV stabilizing properties.

The novel polyoxyalkyleneamine compounds of the present invention are advantageously employed in polyurea, epoxy, and polyurethane systems and exhibit favorable stabilizing properties against degradation, discoloring, etc., caused by light, heat and/or oxidation.

Polyurea elastomer systems are generally prepared by reacting an isocyanate with an active hydrogen component in the presence of a chain extender, as is known by those skilled in the art. The novel compounds of this invention, because of the presence of the highly reactive amine groups which react directly into the polymer network, function well as the active hydrogen component and, advantageously, exhibit the stabilizing properties discussed above. Typically the isocyanate and compound of this invention are reacted in stoichiometric quantities.

Epoxy resin systems are generally prepared by reacting an uncured epoxy resin with one or more curing agents. A wide variety of epoxy resins can be used in the practice of this invention. They are typically described as polyepoxides having an average of about 1.8 reactive 1,2 epoxy groups per molecule. These polyepoxides can be monomeric or polymeric, saturated or unsaturated, aliphatic, cycloaliphatic, aromatic or heterocyclic, and may be substituted with hydroxyl groups, ether radicals, aromatic halogen atoms and the like.

Preferred polyepoxides are glycidyl ether or diglycidyl ether derivatives made by epoxidizing the corresponding alkyl ether or reacting, by known procedures, a molar excess of epichlorohydrogen and an aromatic polyhydroxy compound, such as isopropylene bisphenol, novolak, etc. The epoxy derivatives of methylene or isopropylene bisphenol are preferred. The diglycidyl ether of bisphenol (Epon 828 available from Shell Chemical Co.) is used in the examples which follow.

The polyepoxides disclosed in U.S. Pat. No. 4,316,991 are particularly well suited. Specifically, these include the resinous epoxy polyethers obtained by reacting an epihalohydrin, such as epichlorohydrin, and the like, with either a polyhydric phenol or a polyhydric alcohol. An illustrative, but by no means exhaustive, listing of suitable dihydric phenols includes:
4,4'-isopropylidene bisphenol,
2,4'-dihydroxydiphenylethylmethane,
3,3'-dihydroxydiphenyldiethylmethane,
3,4'-dihydroxydiphenylmethylpropylmethane,
2,3'-dihydroxydiphenylethylphenylmethane,
4,4'-dihydroxydiphenylpropylphenylmethane,
4,4'-dihydroxydiphenylbutylphenylmethane,
2,2'-dihydroxydiphenylditolylmethane,
4,4'-dihydroxydiphenyltolylmethylmethane and the like.

Other polyhydric phenols which may also be co-reacted with an epihalohydrin to provide these epoxy polyethers are such compounds as resorcinol, hydroquinone, substituted hydroquinones, e.g., methylhydroquinone, and the like.

Appropriate curing agents can generally include primary aliphatic amines with an amine functionality of two or more. Particularly preferred are the JEFFAMINE® series of polyoxyalkyleneamines available from Texaco Chemical Company; they include JEFFAMINE D-230, JEFFAMINE T-403, JEFFAMINE D-400, JEFFAMINE D-200 and mixtures thereof. These polyoxyalkylene amines are described with particularity in Texaco Chemical Company's product brochure entitled THE JEFFAMINE POLYOXYALKYLENEAMINES.

Optionally, the epoxy resin formulations of the invention can include an "accelerator" to speed the amine cure of the epoxy resin, especially at ambient temperatures. In several applications, such acceleration is beneficial. Many accelerators are known in the art which can be utilized in accordance with the instant invention. Examples include salts of phenols; salicylic acid salts, amine salts of fatty acids such as those disclosed in U. S. Pat. No. 2,681,901; and tertiary amines such as those disclosed in U. S. Pat. No. 2,839,480. A preferred accelerator in accordance with the instant invention is disclosed in U. S. Pat. No. 3,875,072 issued to G. Waddill, Apr. 1, 1975. The accelerator comprises a combination of piperazine and an alkanolamine in a weight ratio of about 1:8 to 1:1.

Other ingredients such as fillers, pigments and plasticizers may be routinely added to formulations of the invention without detrimental effect upon the invention.

In accordance with one embodiment of the present invention, the epoxy resin system described above further includes from about 1.5 to about 10 percent by weight of the compound of the present invention in order to impart the resulting epoxy system with improved stability toward heat and light degradation, as well as oxidation.

The following Examples I-XV are provided to illustrate specific embodiments of the present invention; they should not be construed as limiting the present invention in any way.

EXAMPLE I

In this example, a propylene oxide adduct corresponding to (I) shown and described above was prepared. Specifically, 300 grams of 2,2,6,6,-tetramethyl-4-aminopiperidine (TMAP) was charged into a one-half gallon stirred autoclave which was then purged with prepurified nitrogen. The reactor was then heated to 115° C. and propylene oxide (PO) addition was commenced. A total of 335 grams PO was then added at 115-125° over a three-hour period. After digestion to an equilibrium pressure, the reaction mixture was vacuum and nitrogen stripped at 125-135° C. to remove unreacted PO. A total of 110 grams unreacted PO was recovered indicating that the TMAP had reacted with two (2) moles PO. The resulting product was a light yellow crystalline material which had the properties shown below in Table I.

TABLE I

| Properties | Results |
|---|---|
| Hydroxyl no. (mg KOH/g) | 595 |
| Total amine (meq/g) | 7.13 |
| Primary amine (meq/g) | 0.073 |
| Secondary amine (meq/g) | 0.448 |
| Tertiary amine (meq/g) | 6.61 |
| Melting point (°C.) | 129-132 |

The 13$^C$ NMR spectra was consistent with the following structure:

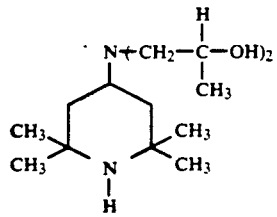

EXAMPLE II

In this example, a 115 hydroxyl number propylene oxide adduct of TMAP was prepared. Specifically, 100 grams TMAP was charged into a one-half gallon stirred autoclave which was then purged with prepurified nitrogen. The reactor was then heated to 125° C. and 82 grams PO was added over a one-hour period. The reaction mixture was then digested two hours to an equilibrium pressure and then stripped under vacuum and nitrogen to remove lights. Potassium hydroxide (2.8 grams) was then charged into the reactor and stirred for 30 minutes until it was solubilized. PO (789 grams) was then reacted at 115°-140° C. and 60-70 psig over an 8.2-hour period. The PO addition was started at 140° C. and was gradually lowered as the reaction proceeded. After digestion to an equilibrium pressure, the product was neutralized by stirring for two hours at 95° C. with 22.4 grams magnesium silicate which was added as an aqueous slurry. Di-t-butyl p-cresol (1.2 grams) was added to stabilize the product. The neutralized product was then vacuum stripped to a minimum pressure, nitrogen stripped, and filtered. The finished product had the properties shown below in Table II.

TABLE II

| Properties | Results |
|---|---|
| Amine (meq/g) | 1.07 |
| Hydroxyl no. (mg KOH/g) | 115 |
| Water (wt. %) | 0.01 |
| pH in 10:6 isopropanol-water | 12.2 |
| Color (Pt—Co) | 50 |
| Sodium (ppm) | 1.2 |
| Potassium (ppm) | 2.6 |
| Viscosity (cs) (77° F.) | 472 |
| (100° F.) | 207 |

EXAMPLE III

This example illustrates the amination of the propylene oxide adduct prepared in Example II to produce the novel polyoxyalkyleneamine compound of this invention. Specifically, a 300-ml stirred autoclave was charged with 150 grams of the adduct produced in Example II, ammonia (23.8 grams), a Raney Ni catalyst (20 grams) and 600 psi hydrogen. The autoclave was heated to 230-242° C. for over one-hour reaction time. Pressure declined from 2350 to 2050 psi during this time. The reactor was cooled to room temperature, vented, and the contents filtered and stripped. The compound produced in this example was analyzed; the results are reported below in Table III.

TABLE III

| Properties | Results |
|---|---|
| Total acetylatables | 1.64 (meq/g) |
| Total amines | 1.59 (meq/g) |
| Primary amine | 0.66 (meq/g) |
| Tertiary amine | 1.10 (meq/g) |

EXAMPLE IV

In this example, another inventive polyoxyalkyleneamine compound was prepared by substantially following the procedure of Example III. In particular, the 300-ml stirred autoclave was charged with 150 grams of the adduct produced in Example II, ammonia (34.3 grams), a catalyst (Ni/Cu/Cr/Mo/Al$_2$O$_3$, 20 grams), and 700 psi of hydrogen. The reaction conditions were 230-242° C. for approximately 3 hours. During the reaction period, the pressure dropped from 3000 to 2350 psi. The reactor was cooled to room temperature, vented, and the product was obtained through the procedures of filtration and stripping. The colorless product mixture was analyzed; the results are reported below in Table IV.

TABLE IV

| Properties | Results |
|---|---|
| Total acetylatable | 1.98 (meq/g) |
| Total amine | 1.93 (meq/g) |
| Primary amine | 1.26 (meq/g) |
| Tertiary amine | 0.98 (meq/g) |
| Color | 30 (Pt/Co) |

With respect to the product produced in Example IV, assuming the starting diol was converted into primary amine product, the conversion was calculated to be = 64% (i.e., 1.26÷1.98). The $^{13}$C NMR indicated the presence of —CH—NH$_2$ (59%) and —CH—OH (41%). It is, therefore, concluded the alcohol was converted into primary amine at approximately 60% conversion with no significant side reactions.

EXAMPLE V

In this example, another inventive polyoxyalkyleneamine compound was prepared by substantially following the procedure of Example III. In particular, the 300-ml stirred autoclave was charged with 150 grams of the adduct produced in Example II, ammonia (20 grams), a catalyst (Ni-Cu-Cr, 20 grams) and H$_2$, ~700 psi. The reaction conditions were 230°-248° C. for two hours. The resulting product, a substantially colorless liquid, was analyzed; the results are reported below in Table V.

TABLE V

| Properties | Results |
|---|---|
| Total acetylatables | 1.52 (meq/g) |
| Total amine | 2.00 (meq/g) |
| Primary amine | 1.31 (meq/g) |
| Tertiary amine | 1.02 (meq/g) |
| Color | 40 (Pt/Co) |

EXAMPLE VI

In this example, another inventive polyoxyalkyleneamine compound was prepared by substantially following the procedure of Example III. In particular, the 300-ml stirred autoclave was charged with 150 grams of the adduct produced in Example II, 33.3 grams of ammonia, 25 grams of Raney Ni catalyst, and approximately 600 psi of hydrogen. The conditions were 230°-257° C. over two hours under pressure of 3400-2700 psig. The resulting product was analyzed; the results are reported below in Table VI.

TABLE VI

| Properties | Results |
|---|---|
| Total acetylatables | 1.59 (meq/g) |
| Total amine | 1.77 (meq/g) |
| Primary amine | 1.13 (meq/g) |
| Tertiary amine | 0.93 (meq/g) |

EXAMPLE VII

In this example, another inventive polyoxyalkyleneamine compound was prepared by substantially following the procedure of Example III. In particular, the 300-ml stirred autoclave was charged with 120 grams of the adduct produced in Example II, 40 grams of ammonia, 30 grams of Raney catalyst, and approximately 600 psi of hydrogen. The reaction conditions were 230° C. for two hours. The resulting product was analyzed; the results are reported below in Table VII.

TABLE VII

| Properties | Results |
|---|---|
| Total acetylatables | 1.51 (meq/g) |
| Total amine | 1.89 (meq/g) |
| Primary amine | 1.19 (meq/g) |
| Tertiary amine | 1.02 (meq/g) |
| Viscosity | 396 (cs/77° F.) |

EXAMPLES VIII-XI

In each of Examples VIII-XI, a cured epoxy resin formulation was prepared by combining the components identified below in Table VIII. The relative amount of each component used is given in parts by weight. In Examples IX, X and XI, the TMAP polyoxyalkyleneamine compound used is that produced above in Example VII.

TABLE VIII

| | Example | | | |
|---|---|---|---|---|
| Component | VIII | IX | X | XI |
| Epoxy resin (EEW) ~188 | 100 | 100 | 100 | 100 |
| JEFFAMINE ® D-230 | 25 | 25 | 25 | 25 |
| Nonylphenol | 26 | 26 | 26 | 26 |
| N-Aminoethylpiperizine | 4 | 4 | 4 | 4 |
| TMAP Polyoxyalkyleneamine | — | 1.6 | 4.8 | 8.2 |

Each of the cured epoxy resin formulations prepared in Examples VIII-XI were evaluated to determine the initial Yellowing Index (YI) and the YI after twenty-four (24) hours, forty-eight (48) hours and seven (7) days of outdoor exposure. The YI was determined in accordance with the ASTM's Standard Test Method for Yellowness Index of Plastics. In all cases, the epoxy resin formulation was applied as a 6 mil clear coating on a white tile. The YI differential (ΔYI) between the initial YI and that after the respective lapsed time periods was also determined. The results of the foregoing evaluations are provided below in Table IX.

TABLE IX

| | Example | | | |
|---|---|---|---|---|
| | VIII | IX | X | XI |
| YI (initial) | 5.28 | 6.17 | 6.04 | 6.00 |
| YI (24 hours) | 29.58 | 26.60 | 19.85 | 14.64 |
| Δ YI | 24.30 | 20.43 | 13.81 | 8.44 |
| YI (48 hours) | 41.01 | 38.02 | 30.31 | 22.82 |
| Δ YI | 35.73 | 31.85 | 24.27 | 16.62 |
| YI (7 days) | 50.77 | 48.70 | 43.99 | 37.49 |
| Δ YI | 45.49 | 42.53 | 37.95 | 31.29 |

As these data demonstrate, the epoxy resin formulation prepared in Example VIII, which didn't contain any TMAP polyoxyalkyleneamine, yellowed after only a short period of outdoor exposure. Addition of increased amounts of the TMAP polyoxyalkyleneamine compound resulted in an increasingly lowered degree of yellowing.

EXAMPLES XII-XV

In each of Examples XII-XV, a cured epoxy resin formulation was prepared by combining the components identified below in Table X. The relative amount of each component used is given in parts by weight. In Examples XIII, XIV and XV, the TMAP polyoxyalkyleneamine compound used is that produced above in Example VII.

These examples show that the addition of the TMAP polyoxyalkyleneamine compound to a non-yellowing weather resistant formulation based on Eponex 1510 (a hydrogenated diglycidyl ether of Bisphenol A - Shell Chemical Co.) even further improves that system.

TABLE X

| Component | Example | | | |
|---|---|---|---|---|
| | XII | XIII | XIV | XV |
| Eponex 1510 | 100 | 100 | 100 | 100 |
| Titanium dioxide | 20 | 20 | 20 | 20 |
| Jeffamine ® T-403 | 42 | 42 | 42 | 42 |
| TMAP Polyoxyalkyleneamine | — | 1.6 | 4.8 | 8.2 |
| Beetle 216-8 (Am.Cyan.) | 1.6 | 1.6 | 1.6 | 1.6 |

Each of the cured epoxy resin formulations prepared in Examples XII-XV were evaluated by the accelerated weathering test described below to determine the initial Yellowing Index (YI) and the YI after four (4) hours, eight (8) hours, twenty-four (24) hours, and forty-eight (48) hours of outdoor exposure. The YI was again determined in accordance with the ASTM's Standard Test Method for Yellowness Index of Plastics. The procedure was followed with Q-U-V accelerated test apparatus as described in ASTM Test Method G53-84. Rapid acceleration of yellowing was achieved by exposing test panels to full UV light for the duration of the test. No water was supplied to the chamber during the period of testing. Thus, the effects of condensation were not measured. The YI differential ($\Delta$YI) between the initial YI and that after the respective lapsed time periods was also determined. The results of the foregoing evaluations are provided below in Table XI.

TABLE XI

| | Example | | | |
|---|---|---|---|---|
| | XII | XIII | XIV | XV |
| YI (initial) | 0.46 | −0.40 | −1.06 | −0.46 |
| YI (4 hours) | 0.74 | −0.82 | −1.64 | −0.56 |
| $\Delta$ YI | 0.28 | −0.42 | −0.58 | −0.10 |
| YI (8 hours) | 0.98 | 0.34 | −0.35 | 0.52 |
| $\Delta$ YI | 0.52 | 0.74 | 0.71 | 9.98 |
| YI (24 hours) | 2.34 | 2.87 | 2.30 | 2.40 |
| $\Delta$ YI | 1.88 | 3.27 | 3.36 | 2.86 |
| YI (48 hours) | 9.30 | 9.97 | 9.23 | 5.71 |
| $\Delta$ YI | 8.84 | 10.37 | 10.29 | 6.17 |

Once again, these data demonstrate that yellowing was found to be more rapid with the epoxy resin formulation prepared in Example XII which is devoid of the TMAP polyoxyalkyleneamine compound. Addition of amounts of the light stabilizer apparently resulted in a bleaching of coatings initially (note negative VI values) and lowered values with formulations containing large amounts of light stabilizer.

What is claimed is:

1. A compound of the formula:

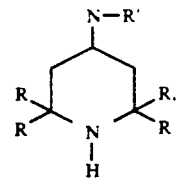

where each of the R groups are the same and R is a $C_1$ to $C_4$ alkyl and R' is either

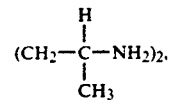

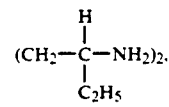

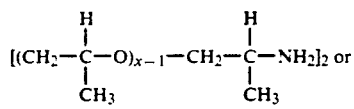

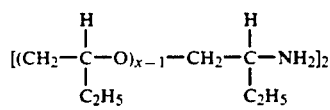

where x is a number from 2 to 10.

2. The compound of claim 1 wherein R is a methyl radical.

3. The compound of claim 1 wherein said compound has a total acetylatable value of from about 1.5 to about 7.5 meg/g.

4. The compound of claim 1 wherein said compound has a total amine value of from about 1 to about 15 meq/g.

5. The compound of claim 1 wherein said compound has a primary amine value of from about 0.5 to about 7.35 meq/g.

6. The compound of claim 1 wherein said compound has a tertiary amine value of from about 0.5 to about 3.7 meq/q.

7. The compound of claim 1 wherein said compound has a molecular weight of about 270 to about 1500.

8. The compound of claim 1 wherein said compound has a molecular weight of about 270 to about 1000.

* * * * *